United States Patent
Chang et al.

(10) Patent No.: US 7,179,867 B2
(45) Date of Patent: Feb. 20, 2007

(54) THERMOSENSITIVE BIODEGRADABLE COPOLYMER

(75) Inventors: Ken-Yuan Chang, Hsinchu (TW); Ming-Hsi Yeh, Chiayi (TW); Ming-Fa Hsieh, Hsinchu (TW); Pei Kan, Hsinchu (TW); Yu-Yan Jan, Tianjhong Township, Changhua County (TW); Shu-Hua Jan, Yongjing Township, Changhua County (TW); Xi-Zhang Lin, Tainan (TW)

(73) Assignee: Industrial Technology Research Institute, Hsinchu (TW)

( * ) Notice: Subject to any disclaimer, the term of this patent is extended or adjusted under 35 U.S.C. 154(b) by 159 days.

(21) Appl. No.: 10/721,877

(22) Filed: Nov. 26, 2003

(65) Prior Publication Data

US 2005/0113531 A1 May 26, 2005

(51) Int. Cl.
*C08L 67/08* (2006.01)

(52) U.S. Cl. ........................ 525/410; 525/415; 525/417

(58) Field of Classification Search .................... None
See application file for complete search history.

(56) References Cited

U.S. PATENT DOCUMENTS

| | | | |
|---|---|---|---|
| 6,004,573 A * | 12/1999 | Rathi et al. ............... | 424/426 |
| 6,117,949 A * | 9/2000 | Rathi et al. ............... | 525/415 |
| 6,541,033 B1 * | 4/2003 | Shah ........................ | 424/486 |
| 6,592,899 B2 * | 7/2003 | Fowers et al. ............ | 424/486 |
| 6,616,941 B1 * | 9/2003 | Seo et al. .................. | 424/450 |
| 6,916,788 B2 * | 7/2005 | Seo et al. .................. | 514/12 |
| 2003/0017206 A1 * | 1/2003 | Seo et al. .................. | 424/486 |
| 2005/0201972 A1 * | 9/2005 | Seo et al. .................. | 424/78.27 |

* cited by examiner

*Primary Examiner*—Kuo-Liang Peng
(74) *Attorney, Agent, or Firm*—Bacon & Thomas, PLLC (57) ABSTRACT

A thermo-sensitve copolymer of following formula;

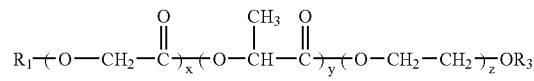

is disclosed; wherein $R_1$ is hydrogen, or $—C(=O)—R_2$; $R_2$ is $C_{7-30}$ alkyl substituted or unsubstituted with functional groups; $R_3$ is hydrogen, or $C_{1-6}$ alkyl; and x, y or z individually is an integer greater than 0. The thermo-sensitive copolymers disclosed here are easy to be implanted into a human body through injection. The biodegradability is greatly improved and the cytotoxicity of the copolymers is low.

5 Claims, 8 Drawing Sheets

The cell is maintained at 37°C.

THERMOSENSITIVE BIODEGRADABLE COPOLYMER

BACKGROUND OF THE INVENTION

1. Field of the Invention

The present invention relates to a biodegradable thermo-sensitive polymer for medical use and, more particularly, to a biodegradable thermo-sensitive polymer for a drug delivery system or embolic agents.

2. Description of Related Art

Several biodegradable polymers have been developed in the past decades for acting as drug release systems for treating chronic diseases in humans. In 1988, Churchill et al. suggested a dispersed polymer for improving the aqueous solubility and the stability of the biodegradable polymers for drug delivery purposes (see U.S. Pat. No. 4,745,160). However, owing to the requirement of dispersity, the application of these biodegradable polymers is limited. For improving the processibility and flexibility of biodegradable copolymers, Song et al. disclosed a multi-block biodegradable copolymer in U.S. Pat. No. 5,514,380. However, since organic solvents are used in the complex manufacturing processes, the application of these biodegradable copolymers continue to be investigated. In 1997, thermosensitive biodegradable tri-block copolymers were disclosed by Cha et al. (see U.S. Pat. No. 5,702,717). These tri-block copolymers are suitable for drug delivery purposes because of their improved biodegradability and high thermo-sensitivity. However, since toxic monomers (e.g. diisocyanates) are used for manufacturing these thermo-sensitive biodegradable tri-block copolymers, the application of these tri-block copolymers in a human body is still limited. Moreover, these thermo-sensitive copolymers illustrated above cannot prevent the bursting out of drugs from the polymeric drug delivery system in a short initial period of drug administration time (burst effect). Therefore, these thermo-sensitive polymers for drug delivery purposes still cannot be widely used.

On the other hand, in some cases, biodegradable polymers functioning as embolic agents for blocking the supply of nutrients to the disordered tissues or cancer cells through arteries are also in demand. However, suitable biodegradable polymers for functioning as embolic agents without toxicity are rare. In addition, the application of the polymeric embolic agents is also limited by the methods for implanting. So far, thermo-sensitive polymers have been suggested to be suitable candidates for embolic agents because of simple implantation (e.g. injection) methods and easy formation of gels. Nevertheless, the toxicity and the biodegradability have become new issues to be solved for these thermo-sensitive polymers. Moreover, thermo-sensitive polymers have also been proposed to be a carrier for biological molecules. For example, copolymers of N-isopropylacrylamide and acrylic monomers were suggested to be used as implantable biohybrid pancreas in which pancreatic islets were encapsulated (see U.S. Pat. No. 5,262,055). However, since poly(NIPAAm) is not a biodegradable polymer, its application in a human body is seriously limited.

In order to achieve the application of thermo-sensitive polymers for functioning as drug delivery systems and embolic agents, it is desirable to provide an improved method to mitigate the aforementioned problems.

SUMMARY OF THE INVENTION

The object of the present invention is to provide a thermo-sensitive polymer having biodegradability and adequate LCST (lower critical solution temperature) to reduce harm to tissues, to simplify the implantation procedures or the manufacturing process, and to reduce the burst effect for drug release.

To achieve the object, the biodegradable block copolymer of the present invention is of the following formula (I):

wherein $R_1$ is hydrogen, or —C(=O)—$R_2$; $R_2$ is $C_{7-30}$ alkyl substituted or unsubstituted with functional groups; $R_3$ is hydrogen, or $C_{1-6}$ alkyl; and x, y or z individually is an integer greater than 0.

Preferably, $R_1$ of the polymer of the present invention is hydrogen, or is selected from the group consisting of cholic acid, fatty acid, folic acid, cholesterol, and vitamin E. More preferably, $R_1$ of the polymer of the present invention is hydrogen or cholic acid (i.e. $R_2$ is of following formula (II):

As $R_1$ is hydrogen, the copolymer of the present invention is a di-block copolymer. The di-block copolymer is suitable for being applied for drug release system or embolic agents. $R_3$ of the copolymer of the present invention can be hydrogen, or $C_{1-6}$ alkyl. Preferably, $R_3$ is methyl. The molecular weight of the present invention is not limited. Basically, the molecular weight of the present invention is the total sum of the hydrophobic block, the hydrophilic block and the acid part. Preferably, the molecular weight of the hydrophobic block:

ranging from 1000 to 6000. The molecular weight of the hydrophilic block:

is preferred to be in a range from 200 to 5000. The ratio of three blocks (i.e. x: y: z) of the present invention is not limited. Preferably, the ratio x: y: z is 3–18:11–66:4–114. The LCST of the copolymer is not limited. Preferably, the LCST of the copolymer ranges from 15° C. to 30° C.

The method for preparing a thermo-sensitive polymer of the present invention, comprising the steps of co-polymerizing a mixture of at least a hydrophilic monomer, at least a hydrophobic monomer and optionally a compound having carboxylic functional group; wherein said hydrophilic monomer is methoxy polyethylene glycol or polyethylene glycol; said hydrophobic monomer is glycolide and lactide, and said compound having a carboxylic functional group is carboxylate having $C_{7-33}$.

The x, y, or z are integers greater than 0. Preferably, the x of the present invention is an integer ranging from 3 to 18. The y is an integer greater than 0. Preferably, y is an integer ranging from 11 to 66. The z is an integer greater than 0. Preferably, z is an integer ranging from 4 to 114. The content of said hydrophilic monomer used in the method of the present invention is not limited. Preferably, the weight percentage of said hydrophilic monomer in the mixture of hydrophilic monomer, hydrophobic monomers, and optionally carboxylates ranges from 30 wt % to 60 wt %. The content of said hydrophobic monomer used in the method of the present invention is not limited. Preferably, the weight percentage of said hydrophobic monomer in the mixture of hydrophilic monomer, hydrophobic monomers, and optionally carboxylates ranges from 70 wt % to 40 wt %.

Other objects, advantages, and novel features of the invention will become more apparent from the following detailed description when taken in conjunction with the accompanying drawings.

DETAILED DESCRIPTION OF THE PREFERRED EMBODIMENT

The structure of the polymer of the present invention includes three major subunits: a hydrophobic unit, a hydrophilic unit and a hydrophobic carboxylic unit. The molecular weight of the hydrophilic monomer used for polymerizing the copolymer of the present invention is not limited. Preferably, the molecular weight of the hydrophilic block ranges from 20 to 5000. Most preferably, the molecular weight of said hydrophilic block ranges from 200 to 5000. In addition, the hydrophilic block helps to increase the solubility of the copolymer of the present invention. The hydrophilic unit also assists to increase the LCST of the whole copolymer. Therefore, the LCST of the copolymer of the present invention can be adjusted by adjusting the percentage of the hydrophilic unit. Furthermore, the hydrophobic block of the copolymer of the present invention can be eliminated by hydrolysis in the human body or in mammals after being implanted or injected into human body. In most cases, the LCST of the copolymer of the present invention is below body temperature by adjusting the percentage of the hydrophilic unit.

The hydrophobic unit of the copolymer of the present invention comes from the co-monomers having a poly (lactide-co-glycolide) (PLGA) block. The molecular weight of the hydrophobic block used for copolymerizing the polymer of the present invention is under 8000. Preferably, the molecular weight of the hydrophobic block ranges from 1000 to 6000. The hydrophobic block helps to increase the hydrophobility and the biodegradability of the copolymer of the present invention. Therefore, the biodegradability of the copolymer of the present invention can be greatly improved. In addition, the hydrophobic unit of the copolymer of the present invention also assists to lower the LCST of the copolymer. The LCST of the copolymer of the present invention can be adjusted to below or around body temperature by adjusting the percentage of the hydrophilic unit and that of the hydrophobic unit. Furthermore, most of the hydrophobic unit will be degraded by hydrolysis in a human body.

The carboxylic-based unit provides the hydrophobicity of the copolymer of the present invention and further greatly improves the affinity of the copolymer of the present invention to hydrophobic drug. The carboxylic-based unit can be any conventional carboxylate having 7 to 33 carbons. Preferably, the carboxylic-based unit comes from compounds such as cholic acid, fatty acid, folic acid and cholesterol.

More detailed examples are used to illustrate the present invention, and these examples are used to explain the present invention. The examples below, which are given simply by way of illustration, must not be taken to limit the scope of the invention.

EXAMPLE 1

Preparation of AB-Type Di-Block Copolymer (PEG-PLGA)

The reaction vessel is heated under nitrogen until the temperature reaches 110° C. Then 50.0 g of lactide, 11.36 g of glycolide, 24.02 g of m-PEG, are added into the reaction vessels together. The reaction vessel is kept heated for melting the added monomers. After all the monomers are melted, 0.05% of catalytic $Sn^{2+}$ is added to the reaction vessel. The temperature of the reaction mixture in the reaction vessel is increased to around 160° C. slowly. Then the reaction mixture is stirred and heated at 160° C. for about 9 hours. The mixture is then cooled to room temperature. 80 ml of $CH_2Cl_2$ is added for dissolving the mixture. The $CH_2Cl_2$ solution is dropped into another solution of n-hexane/ether (9/1) and stirred for 3 hours for precipitation. The solution is separated into two phases. The upper liquid is discarded and the bottom liquid is rinsed and cleaned by a fresh solution of n-hexane/ether at least three times. The precipitates are heated at 45° C. for about 2 hours and vacuumed at 45° C. for another 24 hours. 500 MHz $^1$H-NMR, d-chloroform δ 1.58 (d, J=6.5 Hz, H-4), 3.39 (s, —OCH$_3$), 4.29 (m, H-1,2), 4.80 (m, H-5), 5.14 (m, H-3).

The route for synthesizing the di-block copolymer is shown in scheme 1 illustrated below.

EXAMPLE 2

Preparation of ABC-Type Tri-Block Copolymer (PEG-PLGA-FA(C12))

Nitrogen is introduced to a flask (250 ml) for at least 30 min before reaction. A solution of lauric acid is prepared by adding 1.53 g of lauric acid into 30 ml of CH$_2$Cl$_2$. Another solution is prepared by adding 1.58 g of DCC (dicyclohexyl carbodiimide) into 20 ml of CH$_2$Cl$_2$. The CH$_2$Cl$_2$ solution of DCC is added to the CH$_2$Cl$_2$ solution of lauric acid and stirred for 30 min. Another solution of AB-block copolymer is prepared by dissolving 10 g of di-block copolymer obtained from example 1 into 50 ml of CHCl$_3$. Then 1.5 g of triethylamine is added to the CHCl$_3$ solution of AB-di-block copolymer and stirred for 30 min. The CHCl$_3$ solution of AB-di-block copolymer prepared through above procedure is added dropwise to the well-prepared mixture of lauric acid and DCC and stirred for 24 hours.

After the reaction is finished, the precipitate is removed by DCU (dicyclohexylurea). The remaining filtrate is dropped into a solution of n-hexane/ether and stirred. The precipitated is then washed and reprecipitated 3 times. Then the precipitates are heated at 45° C. for about 2 hours and vacuumed at 45° C. for another 24 hours to remove the residual organic solvent.

500 MHz $^1$H-NMR, d-chloroform

δ 0.86 (t, J=6.8 Hz, H-8), 1.23 (m, H-7), 1.58 (d, J=6.5 Hz, H-4), 2.38 (m, H-6), 3.39 (s, —OCH$_3$), 4.29 (m, H-1,2), 4.80 (m, H-5), 5.14 (m, H-3).

The route for synthesizing the tri-block copolymer is shown in scheme 2 illustrated below.

EXAMPLE 3

Preparation of ABC-Type Tri-Block Copolymer (PEG-PLGA-CA)

Nitrogen is introduced to a flask (250 ml) for at least 30 min before reaction. A solution of cholic acid is prepared by adding 6.27 g of cholic acid into 30 ml of 1,4-dioxane. Another solution is prepared by adding 3.16 g of DCC into 20 ml of 1,4-dioxane. The 1,4-dioxane solution of DCC is added to the 1,4-dioxane solution of cholic acid and stirred for 30 min. Another solution of AB-block copolymer is prepared by dissolving 10 g of di-block copolymer obtained from example 1 into 100 ml of 1,4-dioxane. Then 2.0 ml of triethylamine is added to the 1,4-dioxane solution of AB-di-block copolymer and stirred for 30 min.

After the reaction is finished, the precipitate is removed by DCU. The remaining filtrate is dropped into a solution of n-hexane/ether and stirred. The precipitate is then washed and reprecipitated 3 times. Then the precipitates are heated at 45° C. for about 2 hours and vacuumed at 45° C. for another 24 hours to remove residual organic solvent.

500 MHz $^1$H-NMR, d-chloroform

δ 0.67 (s, H-8), 0.87 (s, H-9), 0.97 (d, J=6.8 Hz, H-7), 1.58 (d, J=6.5 Hz, H-4), 2.38 (m, H-6), 3.39 (s, —OCH$_3$), 4.29 (m, H-1, 2), 4.80 (m, H-5), 5.14 (m, H-3).

EXAMPLE 4

Preparation of Hydrogel/Protein Solution

The block copolymers synthesized above were dissolved in D.I. water. 100 mg/mL bovine serum albumin conjugated with FITC (BSA-FITC) solution was added in to the hydrogel solution and the mixture was gently shaken to assure homogeneous mixing of protein throughout the hydrogel solution. The final concentration of the copolymer was in the range of 10–50% (w/w) and the protein concentration was in the range of 0–50 mg/mL. All the materials used in this example were pre-cooled at 4° C. before use. All the steps mentioned above were performed at low temperature, thereby avoiding undesired gel formation during preparation.

EXAMPLE 5

Figure 3:
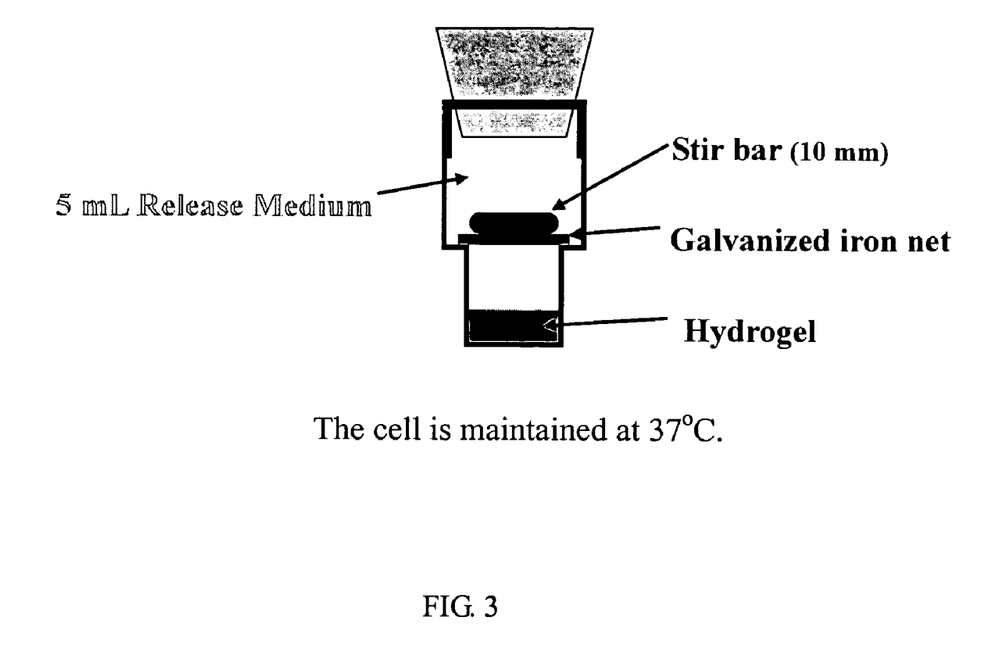
FIG. 3 is a cross-section view of a Release Cell used in example 5.

Drug Release Test 0.2 mL of the hydrogel/BSA solution made from example X was loaded on the bottom of the Release Cell, as shown in FIG. 3. The Release Cell 10 was placed on a Thermstate Module at 37.0±1.0° C. for 10 min. Upon gelation of the hydrogel/BSA solution 50, 5 ml of pre-warmed (37° C.) release medium 20 (phosphate buffer solution) was added into the Release Cell, directly above and in contact with the gel. A galvanized iron net 30 and a stir bar 40 were then mounted in the Release Cell. The releasing test was carried out at 37° C. and the speed was set at 100 rpm. The release medium 20 was replaced with fresh release medium at a predetermined time period. The BSA concentration in the medium was determined by fluorescent spectrophotometer.

Figure 4:
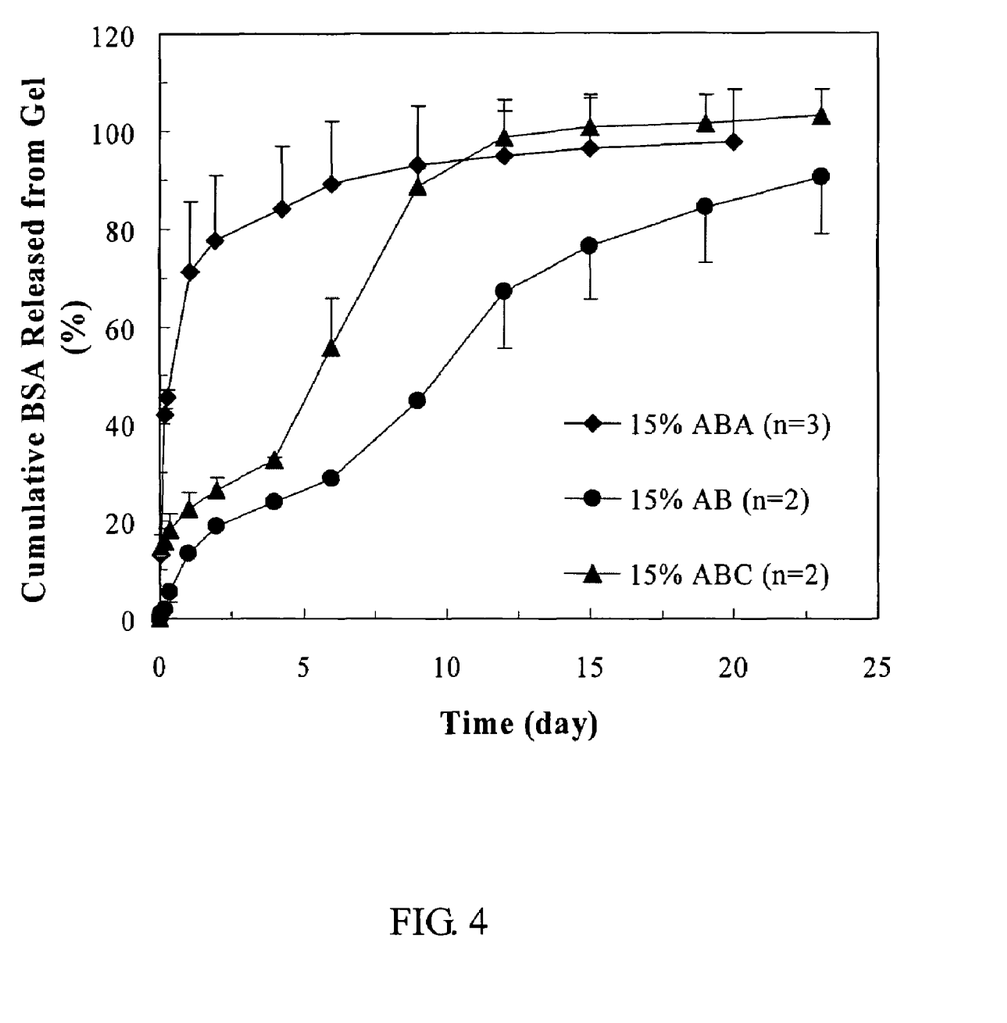
FIG. 4 is a graph of cumulative release from the gel vs. time according to the data in example 5.
Figure 5:
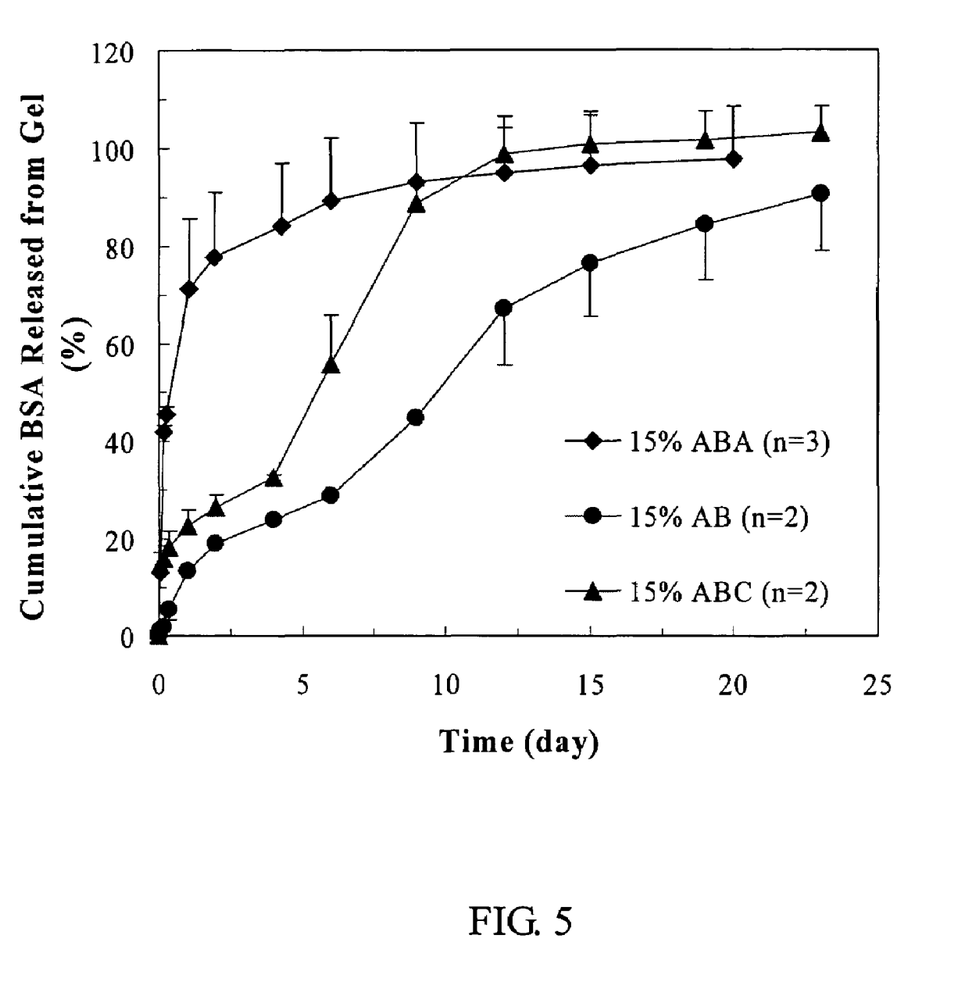
FIG. 5 is another graph of cumulative release from the gel vs. time according to the data in example 5.

According to the results in FIG. 4 and FIG. 5 obtained from the duplicated or triplicated separated experiments, the burst release of BSA was observed in the ABA-type tri-block copolymer hydrogel system. However, the burst release was significantly improved by using the AB-type di-block copolymer and the ABC-type tri-block copolymer hydrogels prepared in examples 1–3.

EXAMPLE 6

Various synthesized hydrogel suspensions of 0.01 g/ml and traditional (AB-type di-block copolymer) hydrogel suspensions of same concentration are provided. These hydrogel suspensions are then diluted to a concentration of 500 μg/ml by adding cell culture medium. The pH of these hydrogel suspensions is adjusted to around 7.4 by adding 1N NaOH. Each hydrogel suspension is laid to a well of a 24-well dish in a volume of 1 ml and further incubated for 1 day. Each hydrogel mixture is taken out through pipettes, Each well is added with MTT (5 mg/ml) and incubated for an additional 2–4 hours. Each well with MTT is taken out through pipettes. DMSO is added to each well until the blue grains are dissolved. After all the blue grains are completely dissolved, the cell viability of each well is analyzed by the absorption of OD 570 nm. The result is listed in FIG. 6.

Figure 6:
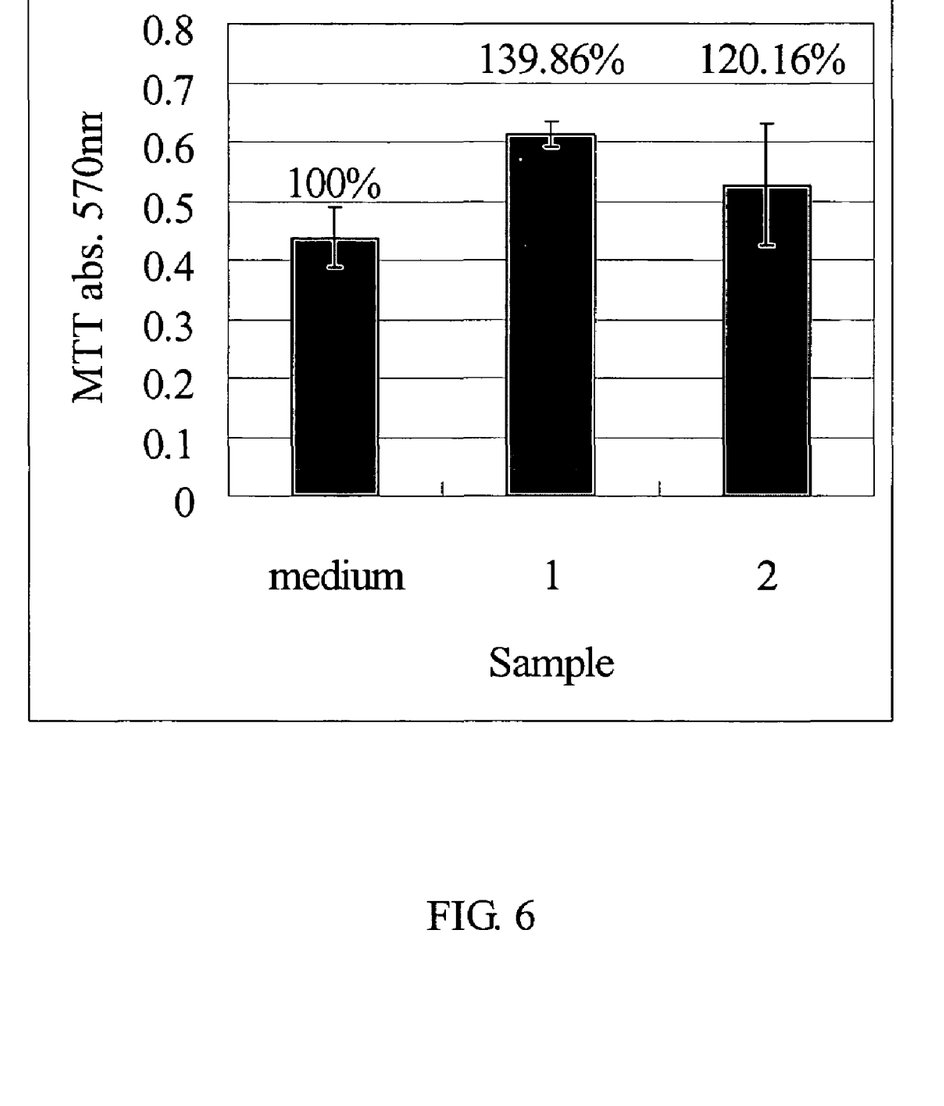
FIG. 6 is a graph of OD 570 absorption of various samples in example 6.

In FIG. 6, the medium represents the cell culture medium without any hydrogel solution. Sample 1 represents PEG-PLGA hydrogel and cell medium_mixture. Sample 2 represents PEG-PLGA-FA(C12) hydrogel and cell medium mixture solutions.

EXAMPLE 7

Figure 7:
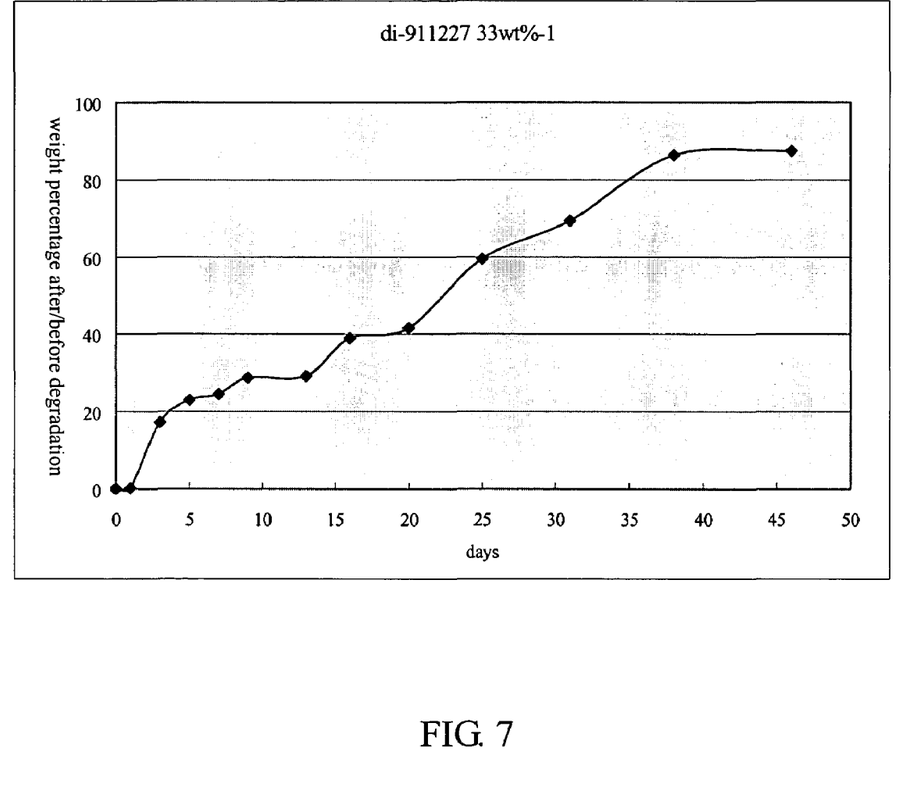
FIG. 7 is another graph of weight percentage before degradation vs. time according to the data in example 6.

Hydrogel samples (AB-type copolymers prepared from example) of various concentrations (25 wt %(di-911227% 33 wt %(di-911227% 20 wt % (di-FA)) are prepared in vials. Each hydrogel sample is stored for a predetermined time (0 day, 1 days, 3 days 5 days, 7 days, 9 days, 13 days, 16 days, 20 days, 25 days, 31 days, 38 days, 46 days). 0.2 ml-of each hydrogel sample of each vial is taken out after the predetermined period and is loaded into a bigger vial (4 ml). Solid gel accompanied with hydrogel liquid may appear after predetermined periods. The weight of each solid gel or hydrogel liquid (not solid gel) can be obtained through weighing and calculation. Then 3 ml of water is added into each bigger vial (4 ml). Each bigger vial is shaken in a water bath at 37° C. and at a rotation speed of 50 rpm. The upper part of liquid in the shaken vial is decanted and the solid gel remaining in the shaken vial is carefully washed with DI water, collected and frozen-dried. The frozen-dried gel is weighed for calculating the reducing weight from degradation. The result is shown in FIG. 7.

EXAMPLE 8

Measurement of the Gel Formation Time In Vitro and the Evaluation of Temperature on Gel Formation The gel formation time is measured by Brookfield DVIII+ cone and plate rheometer. The rheometer is calibrated by various standard solutions (100, 5000 and 10000 cP) first before each measurement. The measurement is performed by placing a tested gel sample (0.5 ml) in the center of a plate at a temperature below 10° C. A thermocouple sensor is mounted under the bottom of the center of the plate for measuring the temperature of the center. A cone #CPD52 is used as the probe in the rheometer.

Warm water at a temperature of 38° C. (or higher than 38° C. but lower than 50° C.) is first introduced into the inner part of the plate at the beginning of measurement. Then the temperature of the plate is heated rapidly to 36–38° C. The related data of viscosity, time, temperature of thermo couple, the rotating speed and the torque of the rheometer are recorded by Rheocalc® (the software specific to the rheometer) from the beginning of and during the measurement. The rotation speed of the rheometer is adjusted so that torque value falls in between 80–100% during the measurement for obtaining reliable experimental data. The gel formation time is defined as the time that a sample needs for increasing the viscosity up to 10000 cP from the starting viscosity.

Figure 1:
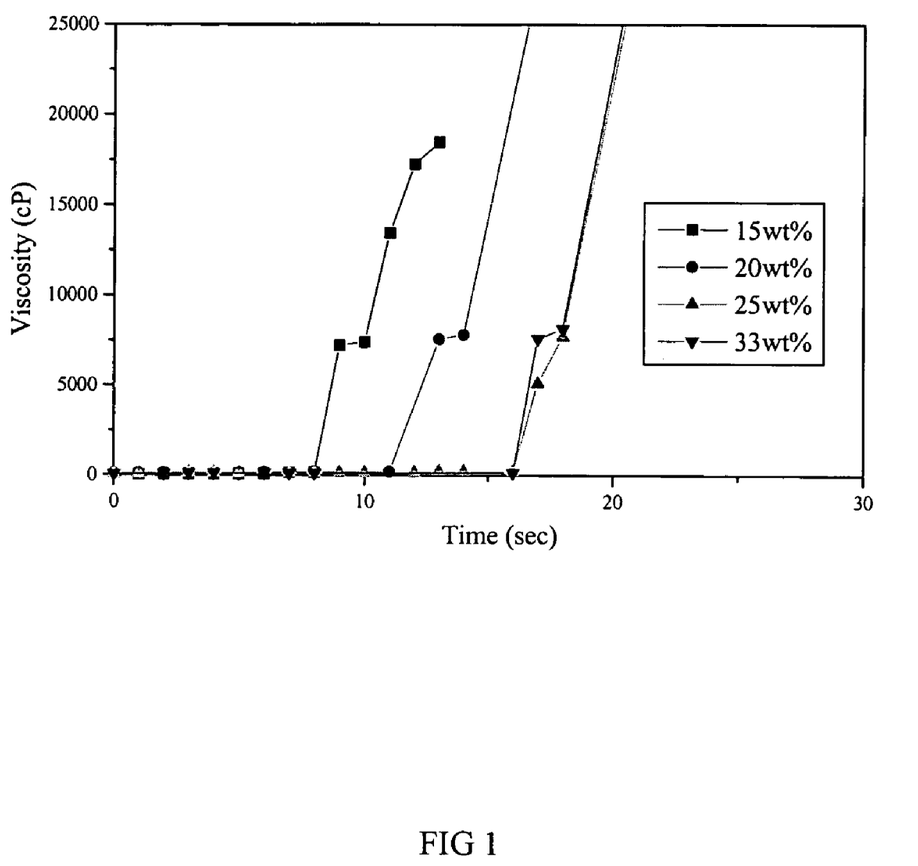
FIG. 1 is the graph of variation of the viscosity in gel samples of 15 wt %. 20 wt %. 25 wt % and 33 wt % in example 8.
Figure 2:
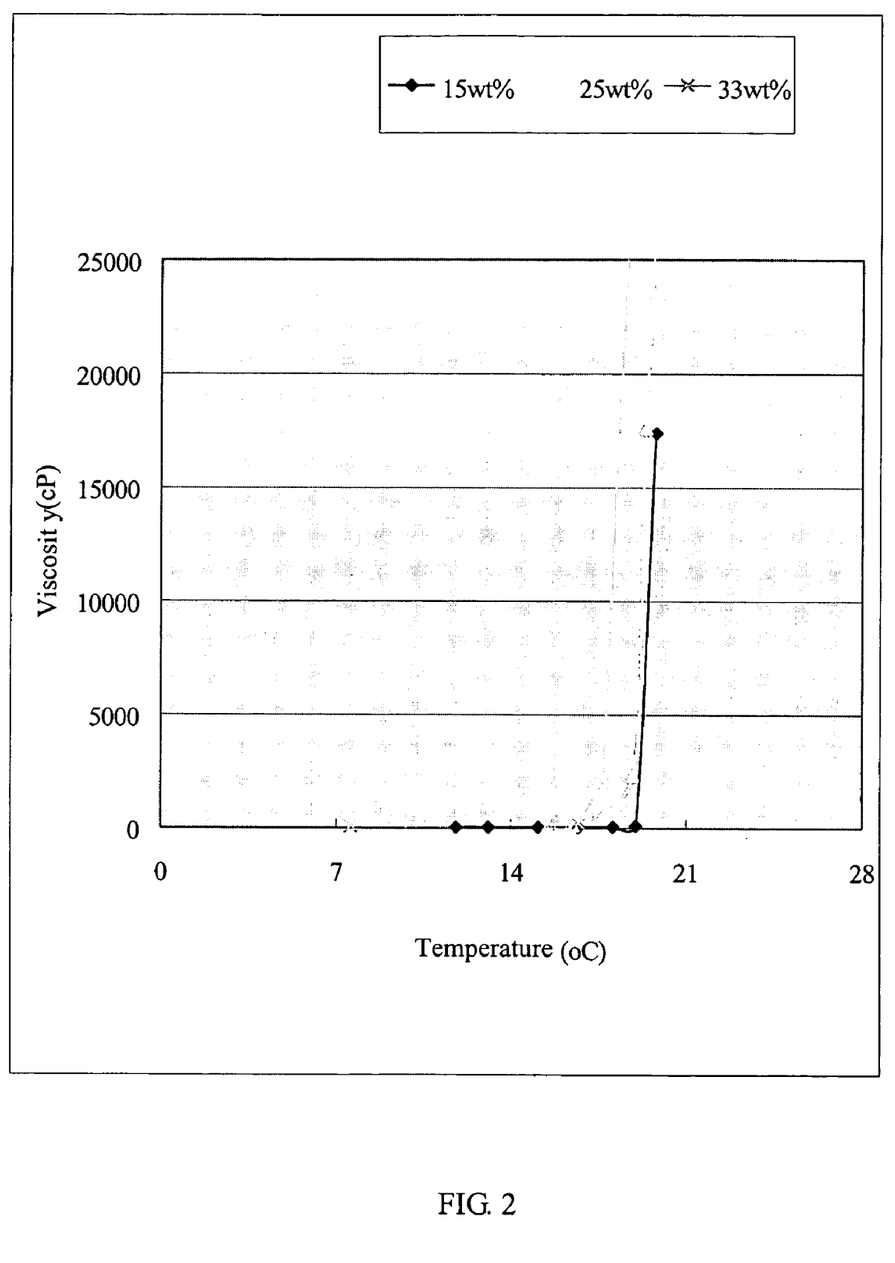
FIG. 2 is the graph of gel viscosity vs. temperature in example 8.

The variation of the viscosity of gel samples of 15 wt %, 20 wt %, 25 wt %, and 33 wt % is shown in FIG. 1. The LCST can be obtained from the graph of gel viscosity vs. temperature. The gelling time can be estimated or obtained by the graph of AB gel viscosity vs. gelling time. As shown in FIG. 1, the gelling time ranges from 10 to 20 seconds. As shown in FIG. 2 the LCST ranges from 15° C. to 30° C.

EXAMPLE 9

Experimental Model of Renal Artery Embolism in a Rabbit

Since the diameter of catheter for a human is larger than the diameter of the hepatic artery of a rabbit; therefore embolism in rabbit renal artery model is used for evaluating the embolism of the thermo-sensitive copolymers of the present invention.

The flow model of the kidney artery is built and recognized though the following method illustrated below. A G22 intravenous catheter is introduced right into the femoral artery of a rabbit. After the needle of intravenous catheter is removed, a guide wire is forced to pass along the femoral artery into the kidney artery. An angiograph catheter is then introduced via the aid of guide wire. A contrast medium, Lipiodol® solution (2 ml/kg dosage), is added through the angiograph catheter after the catheter reaches the renal artery. The distribution and the flow of the contrast medium in femoral artery, aorta and the renal artery can be clearly observed through the assistance of the X-ray photography. According to the observation of the X-ray photography, the developer flowed from the femoral artery to the aorta and further to the renal artery in subsequence. Then the contrast medium stayed in the kidney for a while, after which it backflowed to the heart through the renal vein. The contrast medium then flowed to all the body after the contrast medium was output from the heart.

Figure 8:
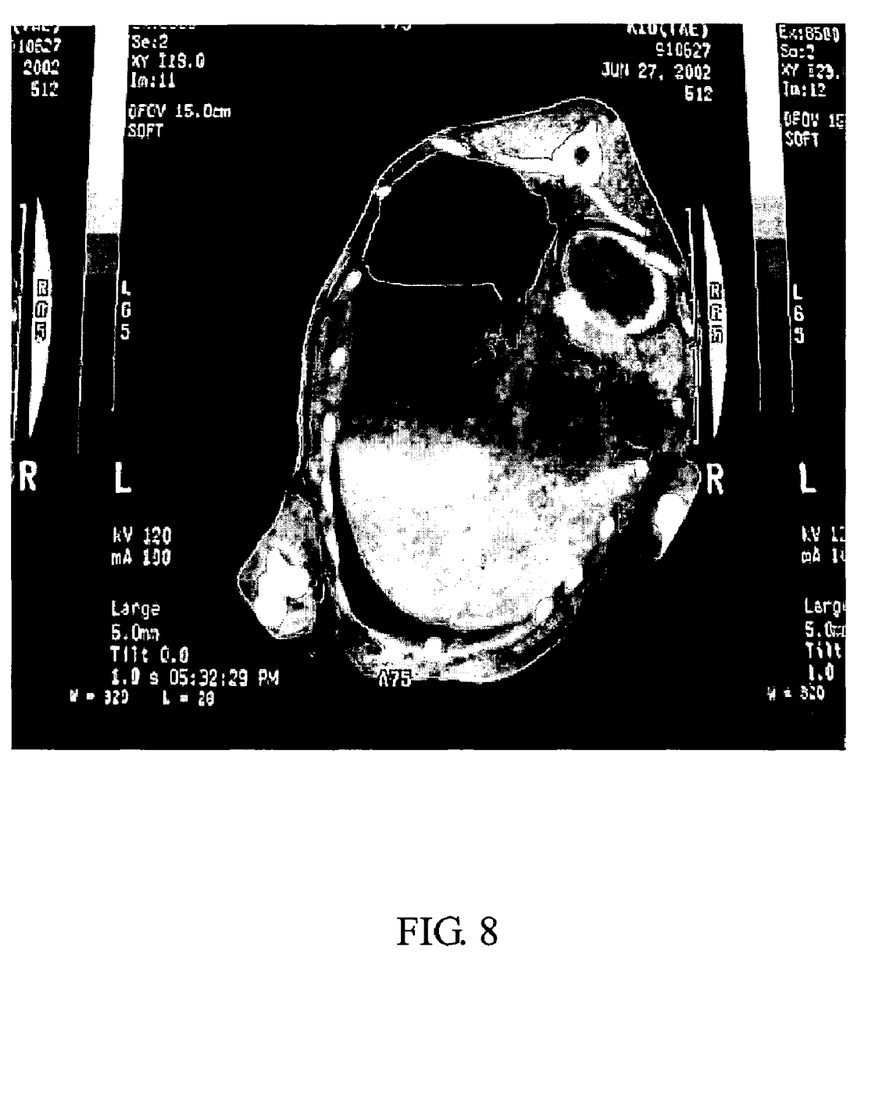
FIG. 8 is a CT photograph of a left kidney in the experimental model of example 9.

Then the distribution of blood vessels is indicated through angiography under the assistance of X-ray. The aqueous solution of thermo-sensitive copolymer of the present invention is prepared in 25% with PBS. The copolymer solution is injected at a predetermined position of the kidney artery for blocking the flowing of blood. After the thermo-sensitive copolymer of the present invention is injected and the embolic surgery is finished, the kidney artery of the rabbit is observed by CT. Once the thermosensitive copolymer solution is injected through the catheter it become gelatinous immediately and blocks blood flow. FIG. 8 demonstrates a dark area in the left kidney in CT photograph which reveals that no blood flow is observed within the kidney. In other words, the injected thermo-sensitive copolymer of the present invention acts as an embolic agent successfully in animal blood vessels.

The thermo-sensitive copolymers of the present invention, both the AB-type and the ABC-type block copolymers, are easy to be implanted into a human body through injection since they contain adequate LCST. In addition, the high biodegradability and the low cytotoxicity of the copolymers of the present invention also make them good candidates for embolic agents or for a delivery system for drugs. Therefore, the copolymer of the present invention is improved greatly in biodegradability and cytotoxicity and is adequate for drug-releasing or embolicing.

Although the present invention has been explained in relation to its preferred embodiment, it is to be understood that many other possible modifications and variations can be made without departing from the spirit and scope of the invention as hereinafter claimed.

What is claimed is:

1. A biodegradable block copolymer of the following formula (I):

wherein $R_1$ is —C(=O)—$R_2$; $R_2$ is selected from the group consisting of cholic acid, fatty acid and folic acid; $R_3$ is hydrogen or $C_{1-6}$ alkyl; x, y or z individually is an integer greater than 0; and said polymer is thermo-sensitive polymer having an LCST ranging from 15° C. to 30° C.

2. The polymer as claimed in claim 1, wherein said $R_3$ is methyl.

3. The polymer as claimed in claim 1, wherein said polymer is applied for drug releasing or embolic agents.

4. The polymer as claimed in claim 1 wherein x: y: z is 3–18:11–66:4–114.

5. The polymer as claimed in claim 1, wherein said polymer is functioned as an embolic agent.

* * * * *